United States Patent
Huang et al.

(10) Patent No.: US 7,144,978 B2
(45) Date of Patent: Dec. 5, 2006

(54) MULTIDROP TREE BRANCHING FUNCTIONAL POLYETHYLENE GLYCOL, METHODS OF PREPARING AND USING SAME

(75) Inventors: Junlian Huang, Shanghai (CN); Michael Min Xu, Shanghai (CN); Xiaojian Hu, Shanghai (CN); Yuhong Xu, Shanghai (CN)

(73) Assignee: Pan Asia Bio Co., Ltd. (CN)

( * ) Notice: Subject to any disclaimer, the term of this patent is extended or adjusted under 35 U.S.C. 154(b) by 0 days.

(21) Appl. No.: 10/891,945

(22) Filed: Jul. 15, 2004

(65) Prior Publication Data
US 2005/0033058 A1    Feb. 10, 2005

(30) Foreign Application Priority Data
Jan. 15, 2002  (CN) ................................. 02 1 01672
Jan. 15, 2003  (WO) ..................... PCT/CN03/00029
Apr. 30, 2004  (CN) ......................... 2004 1 0035191

(51) Int. Cl.
C08G 65/34  (2006.01)
C07D 13/62  (2006.01)
C07D 7/40   (2006.01)

(52) U.S. Cl. ...................... 528/425; 528/328; 528/271; 528/480; 546/300; 548/545; 562/451; 564/504

(58) Field of Classification Search ................ 528/425, 528/328, 271, 480; 546/300; 548/545; 562/451; 564/504
See application file for complete search history.

(56) References Cited

U.S. PATENT DOCUMENTS

| 4,181,770 A | 1/1980 | Schuhmacher ............... 428/260 |
| 5,641,479 A | 6/1997 | Linares et al. ........... 424/70.21 |
| 5,932,462 A | 8/1999 | Harris et al. ................. 435/188 |
| 6,129,912 A | 10/2000 | Hortin et al. ............. 424/93.73 |
| 2003/0219404 A1 | 11/2003 | Yamasaki et al. .......... 424/85.4 |

FOREIGN PATENT DOCUMENTS

WO    WO95/11924    5/2005

OTHER PUBLICATIONS

Bailon et al, Polyethylene glycol conjugates of alpha-interferons, 1997, F. Hoffmann-La Roche A, Switz., Chem Abstact 128: 47304.*
Harris et al, Multi-armed, —and molecules, 1996, Shearwater Polymers, Inc., Chem Abstract 125: 204527.*
Monfardini et al, A branched monomethoxy poly(ethylene glycol) for protein modification, 1995, Bioconjugate Chemistry 6 (1), 62-9, Chem Abstract 122: 75898.*

* cited by examiner

*Primary Examiner*—Duc Truong
(74) *Attorney, Agent, or Firm*—David G. Rosenbaum; Sreenlvasarao Vepechedu; Rosenbaum & Associates, PC (57) ABSTRACT

Multi-armed functional polyethylene glycol polymers with active terminal groups may be used in conjugation with small molecule pharmaceuticals, proteins and peptides to enhance half-life and bioavailability of the drug and improve solubility, stability and immunological competence.

12 Claims, 2 Drawing Sheets

MULTIDROP TREE BRANCHING FUNCTIONAL POLYETHYLENE GLYCOL, METHODS OF PREPARING AND USING SAME

BACKGROUND OF THE INVENTION

The present invention relates generally to the design and synthesis of polymers and macromolecules. In particular, the present invention relates to new class of multiple branched, functional polyethylene glycols. The inventive multiple-branched, functional polyethylene glycols are synthesized by a series of chemical reactions involving linear polyethylene glycols and small molecules to obtain the inventive multiple-branched, functional polyethylene glycols.

There are various types of pharmaceutical drugs, including anti-tumor drugs, which can be classified generally into two categories based on their molecular weights: Type I drugs and Type II drugs. Type I drugs are smaller molecules with relatively lower molecular weights typically less than or equal to about 1 kDa. Most Type I drugs are chemically synthesized or are the result of laborious extraction and purification from naturally occurring sources. Examples of Type I drugs are nitrogen mustards, cis-platinum, 5-fluorouracil, paclitaxel and the like. Type II drugs are macromolecular drugs, most of which are genetically engineered recombinant proteins or peptides. Both Type I and Type II drugs suffer from higher toxicity rates, poor solubility, and relatively lower half life. Furthermore, most proteins and peptides drugs are immunogenic, which may induce harmful immunoreactions.

One of the methods to resolve these problems is through the chemical modification of the drugs with polymers. Caliceti, T. et al., *J. Bioactive Compatible Polym.* 10:103–120 (1995) disclose modification of superoxide dismutase with polyvinyl pyrrolidone. Uren, J. R. et al., *Cancer Res.* V39, 1927–1933, 1981) discloses modification of L-asparaginase with polyDL-alanine. One of the most popular methods of chemically modifying drugs is to use activated polyethylene glycol (PEG) as a drug matrix. For example, Nandini, K et al., European Granted Patent No. EP0247860B2, published Jul. 8, 1992 and Clark, M. A., et al, PCT International Publication No. WO 98/31383 published Jul. 23, 1998, 1998 (PCT/US98/00683) describes the reaction of tumor necrosis factor (TNF) with PEG; Gilbert, C. W et al. U.S. Pat. Nos. 5,951,974, 5,981,709, and 6,042,822 teach using PEG to chemically modify interferon-α. Similar reactions such as modification of interleukin-2 with PEG, Prakash, R. K. et al. U.S. Pat. No. 6,251,866, and PEG modification of granulocyte-macrophage colony-stimulating factor (GM-CSF) with PEG, Knusli, C. et al. *Br. J. Haematl,* 82 (4), 654–663 (1992); Malik, F et al. *Exp. Hemaol,* 20(8), 1028–1035(1992), One of ordinary skill in the art will understand that PEG modification of growth hormones is well known. Each of the foregoing references are hereby incorporated by reference as generally teaching that it is known to PEGylate pharmacologically active agents.

Commonly used active groups in PEG modification of pharmaceuticals, include succinimide active esters, aldehyde group, trifluorsulfonate, p-nitrophenylcarbonate, benzotriazole carbonate etc. Commonly used PEG molecules are either linear or branched monomethoxypoly ethylene glycols with molecular weights ranging from 2–60 kDa, See, e.g., Monfardini, C. et al. *Bioconjugate Chem.* 6:62–69 (1995).

The properties of pharmaceuticals modified by polymers typically depend on a number of factors, including, structure, molecular weight, molecular weight distribution, and configuration of polymer materials used. Therefore, the properties of a PEG-modified drug with the same structure, but with different molecular weights will be different. Furthermore, differences in resulting properties will exist among PEG-modified drugs which have the same structure and molecular weight, but differ in the configuration of the PEG polymers employed. Difficulties have been encountered in PEG-modification of proteins and other pharmaceuticals. Among these difficulties is a lack of conjugating selectivity, which leads to conjugation at active sites of the proteins. This results in a reduction of the bioactivity of the of the drug or protein. Another difficulty is site specific conjugation. For example, some proteins have multiple sites that are susceptible to PEG-modification, which makes site specific PEG modification on such proteins quite difficult. Consequently, quality control is quite difficult for these types of pharmaceutical conjugates.

SUMMARY OF THE INVENTION

Accordingly, it is an object of the present invention to design and synthesize a plurality of multiple branched polyethylene glycol (PEG) polymers having different active and functional terminal groups.

Another object of the present invention is to provide a method for synthesizing multiple branched PEG polymers.

It is another objective of the present invention to provide methods of using the multi-armed PEG polymers of the present invention in conjugation with pharmaceutical agents.

Finally it is an objective of the present invention to provide novel multiple branched PEG polymers having improved physical and chemical properties when compared with linear and branched PEG polymers of like molecular weights known in the art. The inventive multi-armed PEG polymers have been found to have lower static viscosity and greater hydrodynamic volume than conventional branched or linear PEG polymers.

DETAILED DESCRIPTION OF THE PREFERRED EMBODIMENTS

In accordance with the preferred embodiments of the present invention, there is provided a group of new generally linear polyethylene glycol (PEG) polymers that are multiple branched, or, synonymously, multi-armed and functionalized with active groups conjugated at the terminal end of each of the multiple branches.

In accordance with the method of the preferred embodiments of the present invention, there is provided a synthesis of the multi-armed PEG polymers involving a series of reactions of tri-functional small molecules to yield the inventive linear multi-armed PEG polymers.

The inventive PEG polymers are structurally represented by formula I, below:

$$RPEG_zCOX. \quad\quad\quad I$$

Wherein R represents the straight chain alkanes having 1–10 carbon atoms, isopropyl or benzyl groups; z represents the numbers of the branches or arms; X represents a functional group capable of bonding with a biologically active nucleophile selected from the group consisting of proteins, peptides, polypeptides, enzymes and chemotherapeutic molecules or a moiety capable of being functionalized to react with said nucleophile.

Linear polyethylene glycols are linked with small molecules having at least three reactive moieties coupled through a small molecular backbone, wherein the small molecules covalently link the linear PEGs into the multi-armed conformation. Henceforth, these small molecules having at least three reactive moieties are termed "tri-functional small molecules." The at least thee reactive moieties, synonymously "linking groups," between the linear polyethylene glycols (PEGs) and small molecular backbone may be selected from the group consisting of amide, imide, carbamate, ester, epoxy, carboxyl, hydroxyl, thiol, carbohydrate and the combinations of these groups. While the tri-functional small molecules may be selected from a large population of tri-functional molecules, tri-functional small molecules considered especially useful in the present invention are preferably selected from the group consisting of:

where n represents the integer from 1 to 9; m represents the integer from 0 to 6.

For example, when the tri-functional small molecule is $H_2N(CH_2)_nCH(NH_2)CO_2H$ where n is an integer between 1 to 9, and the linking group is amide or carbamate, a new functional PEG polymer with 8 branches, denoted $RPEG_8COX$, is synthesized. The structure of functional PEG polymer with 8 ($RPEG_8COX$) branches is represented by structure II, below:

II where R represents a straight chain alkane having 1–10 carbon atoms, isopropyl, or benzyl groups, with a methyl being preferred; n represents an integer from 1 to 9; k represents an integer from 0 to 6; s, t, o, p each represent an integers from 10 to 2,000; W is one of O, S or NH groups; X is selected from the group consisting of:

The structures of the other multiple branched and functional PEG polymers, e.g., having from 2 to 7 arms, are similar to that of RPEG$_8$COX, with the precise structure, being dependent upon the number of arms. For example, in RPEG$_7$COX, a seven armed PEG polymer, a linear PEG polymer will substitute for one of two branched PEG molecules in RPEG$_8$COX, in RPEG$_6$COX, a single linear polymer will substitute for on of two branched PEG molecules in RPEG$_7$COX. This progression continues until a two-armed linear PEG polymer results. Molecular weights of each arm or branch in the present invention may range from about 400 Da to about 80 kDa.

The synthesis methods of a branched PEG polymer have been reported previously by several groups, e.g. Yamsuki et al. (*Agric Bio. Chem.* (1988), 52, 2185–2196), Monfardini et al. (*Bioconjugate Chem.* (1995), 6, 62–69).

Functionalization or, synonymously, activation of the inventive multi-armed PEG polymers is similar regardless of the number of arms or branches. Similar activation methods are employed among the inventive class of multiple branched PEG polymers having between three and eight PEG polymer branches.

An example of an activation method is illustrated by chemical reactions RxI and RxII, below, which produce, respectively, three armed RPEG$_3$CO$_2$PhHO$_2$ (RxI) and four armed RPEG$_3$CO$_2$PhHO$_2$ (RxII). Activation of linear and branched PEG polymers is consistent with the method reported by Monfardini, et al., infra, which is hereby incorporated by reference.

With Structure II, above as a reference, and where W is NH, n is 4, k is 0, and X is p-nitrophenol, RxI RPEG₄—CO₂PhNO₂

Activation of the carboxylic acid group in the chemical reactions RxI and RxII is achieved through reaction with p-nitrophenol ester, but may be accomplished by using other active esters, such as succinimidyl esters. Where the carboxylic acid group is activated using a succinimdyl ester, it is desirable to protect one amide and one carboxyl group of the tri-functional small molecule in advance. This will permit better control over the resulting molecular weight of each PEG polymer arm.

For example, if the carboxyl acid is activated through succinimidyl ester group, the activations of three armed and four armed PEG polymers can be achieved as illustrated in RxIII and RxIV, below, wherein the (Lys)₂Cu is prepared according to the methods described by S. Wiejak, et al *Chem. Pharm. Bull.* 47, 1489, 1490 (1999), which is hereby incorporated by reference.

Rx III

Rx IV

The foregoing reactions, RxI to RxIV illustrate methods for preparing a wide number of multiple armed PEG polymers having between three and eight branches, with only minor adjustments to the reaction conditions being made, which are within the ordinary skill of the artisan.

The multiple branched and functional PEG polymers of the present invention may be used to chemically modify small molecule pharmacologically active drugs, proteins and peptides. For example, small molecule drugs such as chlorambucil, cis-platinum, 5-fluorouracil, paclitaxel, adriamycin, metrotrexate; protein pharmaceuticals, such as interferon, interleukin, tumor necrosis factor, growth hormone, granulocyte colony-stimulating factor (G-CSF), ethythropoietin (EPO), superoxidedismutase (SOD) are all susceptible of being conjugated or modified with the multi-branched PEG polymer of the present invention.

Conjugation of the inventive multi-branched PEG polymer with small molecular drugs, proteins or peptides may be accomplished by employing well-known methods of conjugating linear PEG polymers disclosed by Greenwald, et al *Bioorg. Med. Chem. Lett.* 4, 2465 (1994); Caliceti, et al., *IL Farmaco*, 48, 919 (1993); and Zalipsky and Lee, *Poly (Ethylene Glycol) Chemistry: Biotechnical And Biomedical Applications*, Harris, J. M., ed., Pleunm Press, N.Y. 1992, each of which are expressly incorporated by reference as teaching conjugation methods with pharmacological agents, and will enable one of ordinary skill in the art to conjugate various pharmacological agents with the multi-branched PEG polymers of the present invention.

Thus, the present invention has been described with reference to its preferred embodiments, and provides a novel class of functional multi-armed PEG polymers having a wide range of molecular weights and which are susceptible of conjugation with a wide variety of pharmacological agents. The inventive functional multi-armed PEG polymers are characterized by having greater hydrodynamic volume than conventional linear or branched PEG polymers of similar molecular weight; by protecting bioactive sites conjugated pharmacological agents such as drugs, proteins and peptides due to steric hinderance; exhibit more highly selective conjugation when compared with conventional linear or branched PEG polymers of similar molecular weights; permitting control and variability of the molecular weight of each PEG polymer branch which allows for control over the hydrodynamic volume of the PEG polymer, which also enhances the bioactivity of conjugated pharmacological agents, proteins and peptides; and due to their multi-branched structure, exhibit a greater ability to hinder macromolecular or cellular interference with the conjugated pharmacological agent, protein or peptide, thereby enhancing the bioavailability of PEG-protein conjugates in the circulation while reducing immunoreactivity of the associated proteins or peptides.

The following examples provide non-limiting examples of the synthesis and use of the present invention in conjugation with pharmacological agents. In each of the following examples, R is methyl group, mPEG is monomethoxypoly (ethylene glycol), GPC is gel penetration chromatography, and MALDI is Matrix-Assisted Laser Desorption/Ionization Mass Spectrum.

EXAMPLE 1

Preparation of Three Branched mPEG$_3$CO$_2$PhNO$_2$ with Different Lengths of Branches Having Arms with Molecular Weights of 7 kDa, 3 kDa and 5 kDa, Respectively 439 mg lysine (3 mmol) was resolved into 20 ml water (pH 8.0 to pH8.3). Then 10 g (0.1 mmol) mPEG$_2$CO$_2$PhNO$_2$ was added in batches. The mPEG$_2$CO$_2$PhNO$_2$ had two branches of the PEG polymer, total molecular weight of 10 kDa, one PEG arm had a molecular weight of 7 kDa, while the other PEG arm had a molecular weight of 3 kDa. The pH of the solution was adjusted to 8.3 with 0.2 N NaOH. The resulting solution was stirred overnight at room temperature then was cooled 0° C. The pH of the reaction products was then adjusted to pH3 with 2N HCl. Impurities were extracted with ether and the residues were triple extracted with chloroform. The resulting extract was concentrated, ether added, and a white precipitate was present. The reaction product of mPEG$_2$-mono-Lysine was then purified by re-crystallization in ethanol. A 99% purity was obtained as characterized by amine titration, GPC and MALDI MS. The protocols for amine titration, GPC and MALDI MS which were followed is found at Monfardini, C., et al. "A Branched Monmethoxypoly(ethylene glycol) for Protein Modification," *Bioconjugate Chem.*, (6) 62–69 (1995)

9 g of mPEG$_2$-mono-Lysine (0.9 mmol) from above reaction was resolved in 20 ml dried dicholormethane, and the pH of the solution was adjusted to pH8 with triethylamine (TEA). 5.025 g mPEGCO$_2$PhNO$_2$ (1.05 mmol, a linear PEG having a molecular weight of 5 kDa) was added into the solution in batches within 3 hours, and the solution pH was maintained at about 8 with TEA. The solution was refluxed for 72 hours, and was cooled down to room temperature. The solution was concentrated, then filtrated. The filtrate was poured into ether slowly. Ether was added to precipitate and the mixtures were filtrated, re-crystallized with ethanol. Excess mPEGCO$_2$PhNO$_2$ was stirred to be hydrolyzed overnight in Na$_2$CO$_3$ buffer (pH 9–10). The solution was cooled down to 0° C., and the pH was adjusted to pH3 with 2N HCl. p-nitrophenol in the solution was extracted with ether. The solution was triple extracted with chloroform, then the extract was dried, concentrated and precipitated with dry ether. The product was then re-crystallized with dry ethanol and was purified further with QAE Sephadex A50 column (5×80 cm, elution: borate buffer of pH 8.9) to yield final product, mPEG$_3$CO$_2$H having three arms of molecular weights 7 kDa, 3 kDa and 5 kDa, respectively. The product was characterized by titration of carboxyl, GPC and MALDI. The purity of the product is more than 99%.

9 g (0.6 mmol) PEG with three branches obtained from the above reactions was resolved in 20 ml dry dichloromethane, 0.167 g p-nitrophenol (1.2 mmol) and 0.48 g 1,3-dicyclohexylcarbodiimide (DCC) (1.2 mmol) were added into the solution. The solution was stirred at room temperature overnight, then filtered. The filtrate was concentrated and precipitated with ether, and the products re-crystallized with ethyl acetate to obtain products of mPEG$_3$CO$_2$PhNO$_2$. After hydrolysis of the products in a basic buffer, the content of activated ester (p-nitrophenol anion) was assayed by UV spectrum at 400 nm. The content of activated ester was above 98%.

EXAMPLE 2

Preparation of Branched mPEG$_3$CO$_2$Succinimide Having Three Different Arm Lengths Having Molecular Weights of 7 kDa, 3 kDa, and 5 kDa, Respectively 9 g three branched mPEG$_3$CO$_2$H (0.6 mmol), each arm having a molecular weight of 7 kDa, 3 kDa and 5 kDa, respectively, obtained from Example 1, was resolved in 20 ml dry dichloromethane, and was cooled to 0° C. 0.138 g N-hydroxysuccinimide (1.2 mmol) and 0.48 g of DCC (1.2 mmol) were then added into the cooled solution, and the solution was stirred overnight, and was filtered. The filtrate was precipitated with ether and re-crystallized with ethyl acetate. The purified product was mPEG$_3$CO$_2$succinimide. The purity of activated ester of the product was assayed with the UV spectrum at 260 nm; the value is greater than 98%.

EXAMPLE 3

Preparation of a Four Branched mPEG$_4$CO$_2$PhNO$_2$ (MW 20 kDa) of Different Arm Lengths (MWs: 7 kDa, 3 kDa, 6 kDa and 4 kDa, Respectively).

9 g mPEG$_2$-mono-Lysine (0.9 mmol), with each arm having a molecular weight of 7 kDa and 3 kDa, respectively, from Example 1, was resolved in 20 ml dry dichloromethane, and the pH of the solution was adjusted to 8 with triethylamine (TEA). 10.5 g of another two branched mPEG$_2$CO$_2$PhNO$_2$ (1.05 mmol, one arm of MW 6 kDa and the one of MW 4 kDa) was added into the solution in batches within 3 hours. The pH of the solution was maintained at 8 with TEA. The solution was refluxed for 72 hours, and then was cooled to room temperature. The reaction mixture was then concentrated, filtrated, and precipitated with ether. The crude product was re-crystallized with dry ethanol, then purified on a QAE Sephadex A50 column (5×80 cm, elution: pH 8.9 borate buffer) to obtain a product was four branched mPEG$_4$CO$_2$H polymer of MW 20 kDa having arms of 7 kDa, 3 kDa, 6 kDa and 4 kDa, respectively. The product was assayed by carboxyl titration, GPC, MALDI, and the resulting purity of the four branched PEG molecules was 98.5%.

The activation of this four branched PEG polymer is as following: 12 g four branched mPEG$_4$CO$_2$H (0.6 mmol) was resolved in 25 ml dry dichloromethane. 0.167 g of p-nitrophenol (1.2 mmol) and 0.48 g of DCC (1.2 mmol) was added into the solution. The solution was stirred overnight, and then filtered. The filtrate was concentrated and precipitated with ether. The crude product was re-crystallized with ethyl acetate to get pure mPEG$_4$CO$_2$PhNO$_2$. The purity of this four branched mPEG$_4$CO$_2$PhNO$_2$ was assayed by UV spectrum at 400 nm and was greater than 98%.

EXAMPLE 4

Alternative Preparation of Three Branched mPEG$_3$CO$_2$PhNO$_2$ of Different Arm Length (7 kDa, 3 kDa and 5 kDa in Each Branch)

2 mM Lysine hydrochloride (365 mg) was added into a 2M NaHCO$_3$ solution (2 ml) under stirring, then 2 ml of 0.5M CuSO$_4$ was added into the solution, and the pH was maintained at 8 with borate buffer. 20 g (2 mM) two branched mPEG$_2$CO$_2$Succinimide ester (with one branch of 7 kDa and another of 3 kDa) was introduced into the solution, NaOH was used to maintain the pH of the solution at pH8.0. The solution was stirred for 24 hours at the room temperature and then the reactant was diluted to 100 ml with de-ionized water. The pH of the solution was adjusted to 3 with oxalic acid and then extracted with dichloromethane three times. The extract was concentrated and precipitated with dry ether. The white precipitate was re-crystallized twice with ethanol to obtain $(mPEG_2Lys)_2Cu$.

20 g (2 mM) $(mPEG_2Lys)_2Cu$ was then resolved in 40 ml acetone. 4.2 mM of 8-hydoxy quinoline and 20 ml of 10% $Na_2CO_3$ solution were then added into the solution, and the solution was stirred for 1 hour at room temperature. 10 g (2 mM) of a linear $mPEGCO_2Succinimide$ ester (MW 5 kDa) was added into the solution, and the pH of the solution was maintained at 8.0 with NaOH. The solution was stirred for 4 hours, and filtered. The pH of the filtrate was then adjusted to 3 with oxalic acid and then extracted with dichloromethane three times. The extract was concentrated, and precipitated with the dry ether. The white precipitation was re-crystallized three times with ethanol to get a product of three branched $mPEG_3CO_2H$ of MW 15 kDa (each of three branches having MW of 7 kDa, 3 kDa and 5 kDa, respectively). The product was then purified on a QAE Sephadex A50 column (5×80 cm, elution buffer: pH 8.9 borate buffer) and characterized by titration of carboxyl, GPC and MALDI. The purity of this three branched PEG molecules of MW 15 kDa was more than 99%

Activation of the three branched $mPEG_3CO_2H$ was conducted by resolving 9 g (0.6 mM) of three branched $mPEG_3CO_2H$ in 20 ml dry dichloromethane, which then was cooled to 0° C. 0.138 g N-hydroxysuccinimide (1.2 mmol) and 0.48 g of DCC (1.2 mmol) were then added into the cool solution and stirred overnight. The solution was filtered and precipitated with ether. The crude product was re-crystallized with ethyl acetate to obtain $mPEG3CO_2Succinimide$. The content of the activated ester of the product was assayed by UV spectrum and found to have a purity greater than 98%.

EXAMPLE 5

Preparation of Four Branched
$mPEG_4CO_2Succinimide$ of MW 40 kDa with the Same Length in Each Arm 2 mM Lysine hydrochloride (365 mg) was added into 100 mL borate buffer. 80 g (4 mM) of two branched 20 kDa $mPEG_2CO_2Su$ (10 kDa MW in each branch) was added into the solution while the pH of the solution was maintained at pH8.0 with 0.2 N NaOH. The solution was stirred 24 hours at room temperature and was diluted to 400 ml de-ionized water. The pH of the solution was adjusted to 3 with oxalic acid. Then the solution was triple extracted with dichloromethane. The extract was concentrated and precipitated with dry ether forming a white precipitate. The white precipitate was re-crystallized twice with ethanol to yield a product of crude four branched $mPEG_4CO_2H$. The crude product was then purified on a DEAE Sephadex FF column to obtain purified four branched $mPEG_4CO_2H$. The yield of the purification of this four branched PEG, with each arm having MW 10 kDa was 92%. Purification was confirmed by NMR, GPC and MALDI MS.

The activation of this four branched PEG molecules was performed by resolving 24 g (0.6 mM) of purified four branched $mPEG_4CO_2H$ from above into 20 ml dry dichloromethane, and was then cooled to 0 ° C. 0.138 g (1.2 mM) N-hydroxysuccinimide and 0.48 g (1.2 mM) DCC were added into the cool solution. The solution was stirred overnight, and filtered. The filtrate was precipitated with ether, and re-crystallized with ethyl acetate to get pure four branched $mPEG_4CO_2Succinimide$ ester. The content of activated ester in the product was assayed by UV spectrum, and the purity was greater than 96%.

EXAMPLE 6

Preparation of Eight Branched (80 kDa)
$mPEG_8CO_2Succinimide$ of the Same Arm Length
(MW 10 kDa Each Branch)

An eight branched $mPEG_8CO_2Su$ (total MW 80 kDa) was produced by the method of Example 5 using four branched (40 kDa total MW with each branch of 10 kDa) $mPEG_4CO_2Su$. The final yield of eight branched $mPEG_8CO_2Su$ was 85%.

The following examples illustrate synthesis of multiple branched PEG molecules with the same length of each branch using PEG molecules with the same length branches as well as the synthesis of multiple branched PEG molecules with different length branches using PEG molecules with different length branches.

EXAMPLE 7

Preparation of Five Branched $mPEG_5CO_2Su$ and $mPEG_5CO_2PhNO_2$

The five branched $mPEG_5CO_2PhNO_2$ was produced using the method described in Example 1 above. Three branched $mPEG_3CO_2PhNO_2$ and two branched $mPEG_2CO_2PhNO_2$ were used as the starting material. The final yield of five branched $mPEG_5CO_2PhNO_2$ was 90%.

The five branched $mPEG_5CO_2Su$ was produced using the method described in Example 2 above, and three branched $mPEG_5CO_2Su$ and two branched $mPEG_5CO_2Su$ were used as the starting material. The final yield of five branched $mPEG_5CO_2Su$ was 91%.

EXAMPLE 8

Preparation of Six Branched $mPEG_6CO_2Su$ and $mPEG_6CO_2PhNO_2$

Six branched $mPEG_6CO_2PhNO_2$ was produced using the method described in Example 1 above. Three branched $mPEG_3CO_2PhNO_2$ were used as the starting material. The final yield of six branched $mPEG_6CO_2PhNO_2$ was 89%. Additionally, six branched $mPEG_6CO_2PhNO_2$ was produced using the method described in Example 1 using two branched $mPEG_2CO_2PhNO_2$ and four branched $mPEG_4CO_2PhNO_2$ subsequently as starting material. The final yield of six branched $mPEG_6CO_2PhNO_2$ was 92%.

The six branched $mPEG_6CO_2Su$ was produced using the method described in the Example 2 above, and the final yield of six branched $mPEG_6CO_2Su$ was 88%.

EXAMPLE 9

Preparation of Seven Branched $mPEG_7CO_2Su$ and $mPEG_7CO_2PhNO_2$

The seven branched $mPEG_7CO_2PhNO_2$ was produced using the method described in the Example 1, using three branched $mPEG_3CO_2PhNO_2$ and two branched mPEG$_4$CO$_2$PhNO$_2$ as starting materials. The final yield of seven branched mPEG$_7$CO$_2$PhNO$_2$ was 86%.

The seven branched mPEG$_7$CO$_2$Su was produced using the method described in the Example 2, and the final yield of seven branched mPEG$_7$CO$_2$Su was 87%.

EXAMPLE 10

Preparation of Eight Branched mPEG$_8$CO$_2$Su and mPEG$_8$CO$_2$PhNO$_2$

The eight branched mPEG$_8$CO$_2$PhNO$_2$ was produced by the method described in the Example 1, using three branched mPEG$_3$CO$_2$PhNO$_2$ and two branched mPEG$_5$CO$_2$PhNO$_2$ as starting material. The yield of eight branched mPEG$_8$CO$_2$PhNO$_2$ was 80%. Additionally, eight branched mPEG$_8$CO$_2$PhNO$_2$ was produced by the method described in the Example 1, using four branched mPEG$_4$CO$_2$PhNO$_2$ as starting material. The final yield of eight branched mPEG$_8$CO$_2$PhNO$_2$ was 79%.

Eight branched mPEG$_8$CO$_2$Su was produced by the method described in the Example 2, and the yield of eight branched mPEG$_8$CO$_2$Su was 78%.

EXAMPLE 11

Multiple armed and functional PEG polymers having 2, 3, 5, 6, 7 and 8 arms, respectively, with aldehyde groups were produced employing the methods described in the Examples 1 to 10.

EXAMPLE 12

Multiple armed and functional PEG polymers having 2, 3, 5, 6, 7 and 8 arms, respectively, with carboxyl groups were produced by the methods described in the Examples 1 to 10.

EXAMPLE 13

Multiple armed and functional PEG polymers having 2, 3, 5, 6, 7 and 8 arms, respectively, with amino groups were produced by the methods described in the Examples 1 to 10.

EXAMPLE 14

Multiple armed and functional PEG polymers having 2, 3, 5, 6, 7 and 8 arms, respectively, with succinimide groups were produced by the methods described in the Examples 1 to 10.

EXAMPLE 15

Conjugation of Recombinant Human Interferon with a Three-Armed PEG

Recombinant human α-Interferon (INFα) was conjugated with a three branched PEG polymer, with each branch having MW 5.4 kDa, one branch of MW 5.6 kDa, one branch of MW 2.3 kDa, respectively to yield mPEG$_3$-IFNα having structure III below.

III $$CH_3(OCH_2CH_2)_{122}O-\overset{O}{\overset{\|}{C}}-NH-(CH_2)_4$$
$$CH_2(OCH_2CH_2)_{127}O-\overset{O}{\overset{\|}{C}}-NH\diagdown\overset{}{\underset{}{CH}}-\overset{O}{\overset{\|}{C}}-NH$$
$$CH_3(OCH_2CH_2)_{45}O-\overset{O}{\overset{\|}{C}}-NH\diagup\quad(CH_2)_4O$$
$$O\;CH-\overset{O}{\overset{\|}{C}}-NH-IFN|A$$

A three branched mPEG$_3$CO$_2$Su (MW 13.3 kDa) was prepared according to Example 2 in which a two branched mPEG$_2$CO$_2$PhNO$_2$ (MW 11 kDa; one branch MW 5.6 kDa, the other branch MW 5.4 kDa) and a linear mPEGCO$_2$PhNO$_2$ (MW 2.3 kDa) were used to synthesize the triple branched mPEG$_3$CO$_2$Su.

The three branched mPEG$_3$CO$_2$Su (100 mg) was mixed with 20 mg of recombinant human Interferon (INF)α2b protein (5 mg/mL, 4 mL) in 50 mM phosphate buffer of pH7.0. After one hour, 100 μl of 1 M glycine was added into the solution to stop the reaction. The mixture contained crude mPEG$_3$-IFNα, un-reacted PEG derivatives and unmodified IFNα.

The mPEG$_3$-IFNα in the mixture was purified using a TSK-GEL Super SW3000 column which was equilibrated with 50 mM NaCl solution (pH7.5). A loading sample of about 2% column volume was injected into the column. Elution was monitored by an UV detector at 280 nm. mPEG$_3$-IFNα conjugates were eluted first and collected, followed by un-modified IFNα and followed by residual PEG.

EXAMPLE 16

Conjugation of Recombinant Human Granulocyte Colongy-Stimulating Factor with Triple Branched PEG Recombinant human Granulocyte Colony-Stimulating Factor (G-CSF) was conjugated with a triple branched PEG derivative (MW 15 kDa) of mPEG$_3$CO$_2$Su, with each branch having a molecular weight of 5 kDa as illustrated in structure IV, below:

IV $$CH_3(OCH_2CH_2)_{113}O-\overset{O}{\overset{\|}{C}}-NH-(CH_2)_4$$
$$CH_2(OCH_2CH_2)_{113}O-\overset{O}{\overset{\|}{C}}-NH\diagdown\overset{}{\underset{}{}}C-NH$$
$$CH_3(OCH_2CH_2)_{113}O-\overset{O}{\overset{\|}{C}}-NH\diagup\quad(CH_2)_4\;O$$
$$O\;CH-\overset{\|}{C}-NH-G\text{-}CSF$$

A three branched (MW 15 kDa) mPEG$_3$CO$_2$Su was prepared by the method of described in the Example 2, in which a two branched mPEG$_2$CO$_2$PhNO$_2$ (MW 10 kDa, each branch with MW 5 kDa) and a linear mPEGCO$_2$PhNO$_2$ (MW 5 kDa) were used to synthesize the three branched mPEG$_3$CO$_2$Su (MW 15 kDa).

100 mg mPEG$_3$CO$_2$Su was mixed with 4 mL of 5 mg/mL recombinant G-CSF protein in 50 mM phosphate buffer at pH7.0 for an hour. Then 100 μl of 1 M glycine was added into the solution to stop the reaction and obtain mPEG$_3$-G-CSF, residual PEG and unreacted G-CSF protein.

mPEG$_3$-G-CSF conjugates were purified from the mixture using TSK-GEL Super SW3000 column which was first equilibrated with 50 mM NaCl (pH7.5). A loading sample of about 2% column volume was injected into the column. Elution was monitored by an UV detector at 280 nm with the mPEG$_3$-G-CSF conjugates eluting first which were collected, followed by unreacted G-CSF, then unreacted PEG.

Structural analysis and physical-chemical analysis of purified mPEG$_3$-G-CSF conjugates were determined by MALDI-TOF MS employing the method described by Grace, J. et al. in *J. Interferon and Cytokine Research*, 1103–1115 (2001), which is hereby incorporated by reference.

Figure 1:
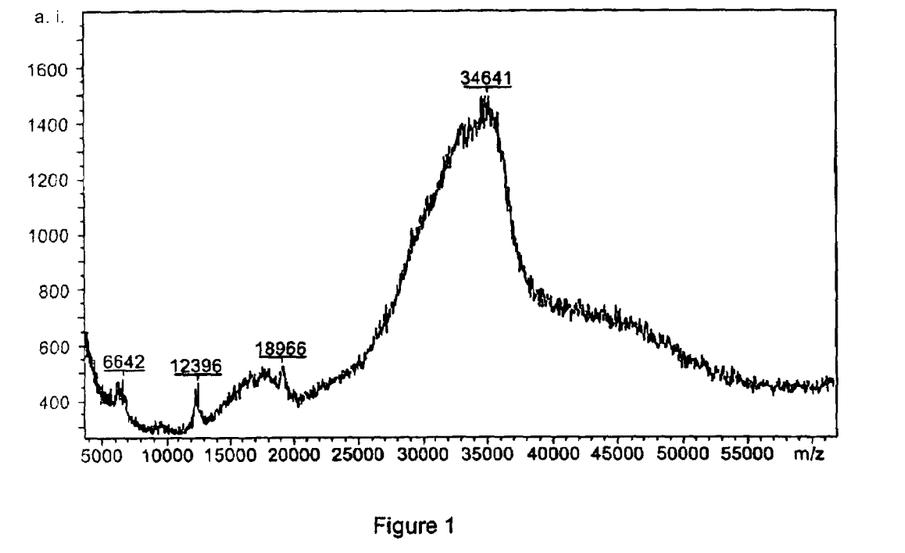
FIG. 1 is a Matrix-Assisted Laser Desorption Ionization Time of Flight Mass Spectroscopy (MALDI-TOF MS) spectrum of mPEG3-G-CSF in accordance with Example 16 of the present invention.

Matrix-Assisted Laser Desorption/Ionization Time of Flight Mass Spectrometry (MALDI-TOF MS) was used to characterize the fractionated mPEG$_3$-G-CSF. FIG. 1 illustrates the obtained MALDI-TOF MS spectrum which shows peaks corresponding to the single charged mPEG$_3$-G-CSF at mass 34641, the single charged trace G-CSF at mass 18966 and the double charged mPEG$_3$-G-CSF at mass 17500. These results indicate that G-CSF was successfully conjugated successfully with the triple branched PEG (MW 15 kDa). The purity the mPEG$_3$-G-CSF was more than 99%.

EXAMPLE 17

Conjugation of Human G-CSF with Four-Armed PEG

Human G-CSF was conjugated with a four branched mPEG$_4$CO$_2$Su (Total MW 10 kDa with each branch of MW 2.5 kDa), with the resulting structure depicted below as structure V:

V

Four branched (MW 10 kDa) mPEG$_4$CO$_2$Su was prepared by the method of described in Example 5 using two double-armed mPEG$_2$CO$_2$Su (MW 5 kDa, each branch of 2.5 kDa) to synthesize four branched mPEG$_4$CO$_2$Su (MW 10 kDa).

100 mg mPEG$_4$CO$_2$Su was mixed with 5 mL of 4 mg/mL G-CSF protein in 50 mM borate buffer (pH6.5) for an hour. Then 50 μl of 1 M glycine was added into the solution to stop the reaction. The mPEG$_4$-G-CSF conjugates were purified by the method described in Example 16.

EXAMPLE 18

Pharmacokinetics Studies of PEG-Protein or PEG-Peptide Conjugates in Rats

Figure 2:
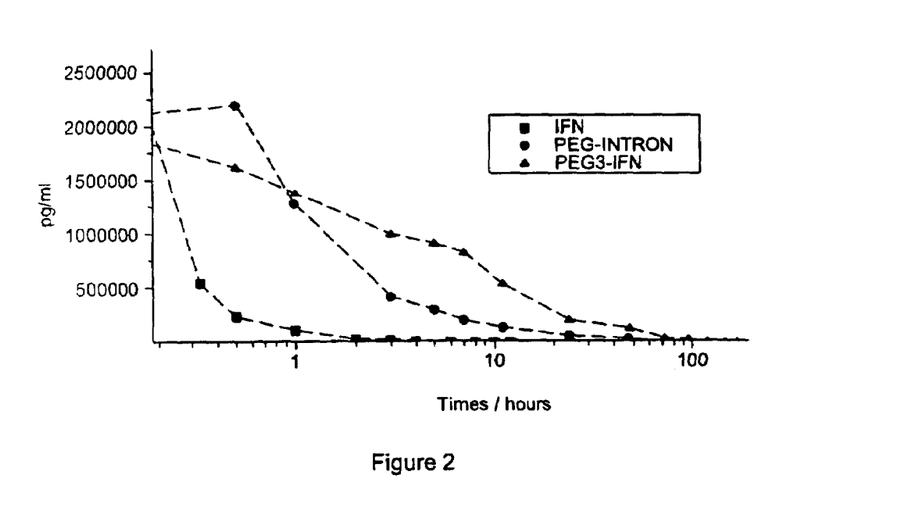
FIG. 2 is a graph of blood plasma concentration over time of IFNα, mPEG$_3$-IFNα, and PEG-INTRON from pharmacodynamic testing of Example 18 of the present invention.

To assess pharmacokinetics of human PEGylated IFNα in rats (average weight of rat is 150~170 g), 400 μg IFN α or mPEG$_3$-IFNα of Example 15 were injected i.v. into the tail vein of each rat. PEG-INTRON (Schering Plough) were used as a positive control. Blood was obtained via retro-orbital bleeds immediately after injection and at 0.25 h, 0.5 h, 1 h, 4 h, 24 h, 36 h, 48 h, 60 h, 72 h, 96 h, 120 h, 144 h, 168 h after dosing. At least three rats were bled at each collection time. Whole blood was collected into tubes containing anticoagulant, cells were removed, and the resulting plasma frozen until the time of assay. FIG. 2 illustrates plasma concentrations of unmodified INFα, PEG-INTRON, and mPEG$_3$-IFNα in the rats over time. Table 1 summarizes the eliminating half life-times which were calculated from the i.v. data. It was found that the average serum half-life of mPEG$_3$-IFNα increased about 4.02 fold over that of unmodified IFNα.

TABLE 1

| The half life-time of mPEG$_3$-IFNα, IFNα, PEG-INTRON | | | |
|---|---|---|---|
| | PEG3-IFNα | PEG-INTRON | IFNα |
| Half life-time (h) | 27.13 | 13.39 | 6.75 |

EXAMPLE 19

Anti-Viral Activity of mPEG3-IFNα

The anti-viral activity of mPEG$_3$-IFNα from Example 15 was assayed using cytopathic effect assay described by Sun, W., "The methods for the study of cytokines," *People's Medical Press*, Beijing, China (1999). The anti-viral activities of unmodified IFNα and mPEG$_3$-IFN were determined to be $3.45 \times 10^7$ IU/mg and $4.0 \times 10^6$ IU/mg, respectively.

EXAMPLE 20

The Pharmacodynamic Study of mPEG$_4$-G-CSG in Mice

To evaluate PEGylated human G-CSF on blood cell counts in mice (average weight 15~20 g), three injections (i.v.) of 250 μg/kg/dose of unmodified human G-CSF though tail vein were made over three consecutive days (one injection/day) to mice in the control group. A single injection of 250 μg/kg/dose (i.v.) mPEG$_4$-G-CSF was given to mice through tail vein in the test group. An equal volume of a phosphate buffer was given to mice as a negative control. Blood from these rats was obtained via retro-orbital bleed. Whole blood was collected at days 1, 2, 3, 4, 5, 6, and 7 after injection. White blood cells were isolated from the whole blood and counted under microscopy.

Figure 3:
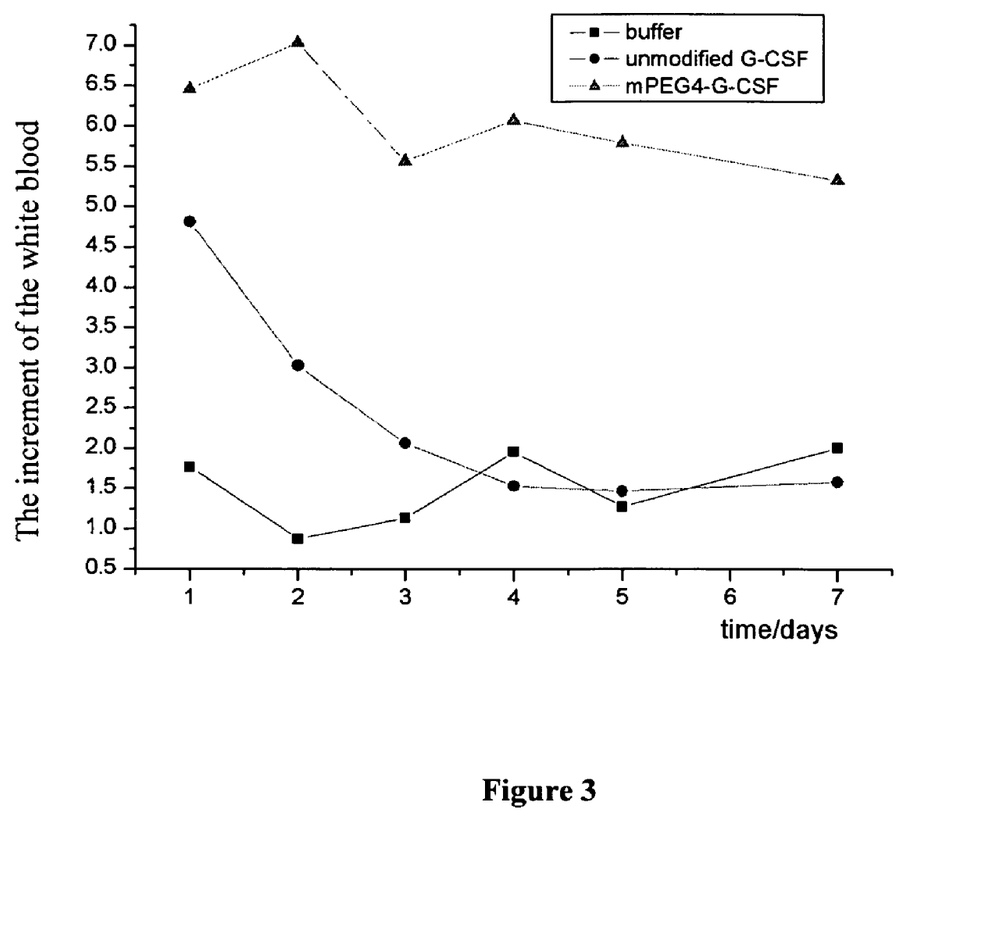
FIG. 3 is a graph of white blood counts over time of unmodified human G-CSF, mPEG$_4$-G-CSF and a buffer negative control in accordance with Example 20 of the present invention.

FIG. 3 charts the effect of unmodified G-CSF and conjugated mPEG$_4$-G-CSF on rat white cell counts at each day of collection. Day 0 is one day before the initial injection day. The increment of the white blood cells on any given day of injection was calculated by the ratio:

$$\frac{\#WBCDayX}{\#WBCDay0}$$

Where WBC is white blood cells and Day X is the injection day.

The mice in the control group that were injected with unmodified human G-CSF showed an increase in WBCs after the last injection, but a decrease at Day 4, attaining the same level as the negative control group at Day 7. In contrast, the mice in the test group exhibited an elevation in WBCs immediately after the single injection of mPEG$_4$-G-CSG. conjugate. At day 7, the WBCs of the test group were 2 to 3 times greater than that of the negative control group at the same time. These results suggest that the mPEG$_4$-G-CSG conjugate has better and longer effects on WBC count than unmodified G-CSF.

While the present invention has been described with reference to its preferred embodiments, those of ordinary skill in the art will understand and appreciate that the present invention is not intended to be limited by these preferred embodiments, and is instead contemplated to include all embodiments consistent with the spirit and scope of the present invention as defined by the appended claims.

What is claimed is:

1. A multi-armed polyethylene glycol, comprising general formula I:

$$RPEG_zCOX \qquad\qquad I$$

wherein, R is a straight-chain alkane containing 1 to 10 carbon atoms, isopropyl or benzyl group; z is 4–8 representing the number of polyethylene glycol arms; and X is a functional group.

2. The multi-armed polyethylene glycol according to claim 1, further comprising at least one linking group selected from the group consisting of amide, imide, carbamate, ester, epoxy, carboxyl, hydroxyl, thiol, and carbohydrate.

3. The multi-armed polyethylene glycol according to claim 1, wherein X is OH.

4. The multi-armed polyethylene glycol according to claim 1, further comprising a conjugate with a pharmacologically active agent.

5. The multi-armed polyethylene glycol according to claim 1, further comprising a conjugate with a biologically active nucleophile.

6. The multi-armed polyethylene glycol according to claim 5, wherein the biologically active nucleophile is selected from the group consisting of proteins, peptides, polypeptides, enzymes and chemotherapeutic agents.

7. The multi-armed polyethylene glycol according to claim 4, wherein the pharmacologically active agent is selected from the group consisting of chlorambucil, cisplatinum, taxol, 5-fluorouracil, paclitaxel, adriamycin, metrotrexate, interferon, interleukin, tumor necrosis factor, growth hormone, granulocyte colony-stimulating factor, ethythropoietin, and superoxidedismutase.

8. The multi-armed polyethylene glycol according to claim 4, wherein the multi-armed glycol is selected from the group consisting of RPEG$_4$-CO$_2$PhNO$_2$, RPEG5-CO$_2$PhNO$_2$, RPEG$_6$-CO$_2$PhNO$_2$, RPEG$_4$-CO$_2$PhNO$_2$, RPEG$_8$-CO$_2$PhNO$_2$, RPEG$_4$CO$_2$Succinimide, RPEG$_5$CO$_2$Succinimide, RPEG$_6$CO$_2$Succinimide, RPEG$_7$CO$_2$Succinimide and RPEG$_8$CO$_2$Succinimide, wherein R is a straight-chain alkane containing 1 to 10 carbon atoms, isopropyl or benzyl group.

9. A multi-armed polyethylene glycol, comprising general formula V, wherein z is 8 representing the number of polyethylene glycol arms, R is a straight-chain alkane containing 1 to 10 carbon atoms, isopropyl or benzyl groups, n is an integer from 1 to 9, k is an integer from 0 to 6, s, t, o, and p are integers from 10 to 2,000, W is O, S, or NH and X is a functional group:

10. The multi-armed polyethylene glycol according to claim 9, wherein X is OH.

11. A multi-armed polyethylene glycol, comprising general formula I:

$$RPEG_zCOX \qquad I$$

wherein, R is a straight-chain alkane containing 2 to 10 carbon atoms, isopropyl or benzyl group; z is an integer representing the number of polyethylene glycol arms; and X is a functional group.

12. The multi-armed polyethylene glycol according to claim 11, wherein the multi-armed glycol is selected from the group consisting of-$RPEG_2$-$CO_2PhNO_2$, $RPEG_3$-$CO_2PhNO_2$, $RPEG_4$-$CO_2PhNO_2$, $RPEG_5$-$CO_2PhNO_2$, $RPEG_6$-$CO_2PhNO_2$, $RPEG_4$-$CO_2PhNO_2$, $RPEG_8$-$CO_2PhNO_2$, $RPEG_3CO_2$Succinimide, $RPEG_4CO_2$Succinimide, $RPEG_5CO_2$Succinimide, $RPEG_6CO_2$Succinimide, $RPEG_7CO_2$Succinimide and $RPEG_8CO_2$Succinimide.

* * * * *

UNITED STATES PATENT AND TRADEMARK OFFICE
CERTIFICATE OF CORRECTION

PATENT NO. : 7,144,978 B2
APPLICATION NO. : 10/891945
DATED : December 5, 2006
INVENTOR(S) : Junlian Huang et al.

It is certified that error appears in the above-identified patent and that said Letters Patent is hereby corrected as shown below:

On The Title Page – Item 75 – Inventors:
    Please delete "Xiaojian" and insert -- Xiao Jian --

Column 2 – Line 19:
    Please delete the second instance "of the"

Column 3 – Line 34:
    Please delete "thee" and insert -- three --

Column 5 – Line 25:
    Please delete "structure," and insert -- structure --

Column 5 – Line 30:
    Please delete "on" and insert -- one --

Column 6 – Line 40:
    In the last line of Chemical Reaction RxI:
    Please delete the Chemical Structure "$RPEG_2\text{-}CO_2PhNO_2$"
    and insert the Chemical Structure -- $RPEG_3\text{-}CO_2PhNO_2$ --

Column 7 – Line 65:
    In the first line of Chemical Reaction RxIV:
    Please delete the Chemical Structure "$2RPEG_3CO_2Su$"
    and insert the Chemical Structure -- $2RPEG_2CO_2Su$ --

Column 9 – Line 17:
    Please delete "cooled 0°" and insert -- cooled to 0° --

Column 14 – Lines 1-13:
    Please delete:

UNITED STATES PATENT AND TRADEMARK OFFICE
CERTIFICATE OF CORRECTION

PATENT NO. : 7,144,978 B2
APPLICATION NO. : 10/891945
DATED : December 5, 2006
INVENTOR(S) : Junlian Huang et al.

It is certified that error appears in the above-identified patent and that said Letters Patent is hereby corrected as shown below:

Column 14 – Lines 1-13: (cont'd)
And Insert:

Column 14 – Lines 50-57:
Please delete:

And insert:

Column 15 – Line 26:
Please delete "purity the" and insert -- purity of the --

Column 15 – Line 58:
Please delete "method of described" and insert -- method described --

Column 16 – Line 53:
Please delete "though" and insert -- through --

UNITED STATES PATENT AND TRADEMARK OFFICE
CERTIFICATE OF CORRECTION

PATENT NO. : 7,144,978 B2
APPLICATION NO. : 10/891945
DATED : December 5, 2006
INVENTOR(S) : Junlian Huang et al.

It is certified that error appears in the above-identified patent and that said Letters Patent is hereby corrected as shown below:

Column 18 – Lines 25-26 in Claim 8:
Please delete "RPEG5-CO$_2$PhNO$_2$" and insert -- RPEG$_5$-CO$_2$PhNO$_2$--

Column 20 – Line 3 in Claim 12:
Please delete "of-RPEG$_2$-CO$_2$PhNO2" and insert -- of RPEG$_2$-CO$_2$PhNO$_2$ --

Signed and Sealed this

Seventeenth Day of July, 2007

JON W. DUDAS
*Director of the United States Patent and Trademark Office*